US012428362B2

(12) United States Patent
Ponsard et al.

(10) Patent No.: US 12,428,362 B2
(45) Date of Patent: Sep. 30, 2025

(54) METHOD FOR PREPARING ACRYLIC ACID FROM BETA-PROPIOLACTONE

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR)

(72) Inventors: Louise Ponsard, Gif-sur-Yvette (FR); Nicolas Lentz, Gif-sur-Yvette (FR); Emmanuel Nicolas, Gif-sur-Yvette (FR); Thibault Cantat, Gif-sur-Yvette (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 539 days.

(21) Appl. No.: 17/926,107

(22) PCT Filed: May 17, 2021

(86) PCT No.: PCT/EP2021/063014
§ 371 (c)(1),
(2) Date: Nov. 17, 2022

(87) PCT Pub. No.: WO2021/233839
PCT Pub. Date: Nov. 25, 2021

(65) Prior Publication Data
US 2023/0192585 A1    Jun. 22, 2023

(30) Foreign Application Priority Data
May 19, 2020   (FR) .................................... 2005098

(51) Int. Cl.
C07C 51/09    (2006.01)
B01J 20/26    (2006.01)
(Continued)

(52) U.S. Cl.
CPC ............. *C07C 51/09* (2013.01); *B01J 20/264* (2013.01); *B01J 20/28038* (2013.01);
(Continued)

(58) Field of Classification Search
CPC ........ C07C 51/09; C07C 51/44; B01J 20/264; B01J 20/28038; B01J 20/321;
(Continued)

(56) References Cited

U.S. PATENT DOCUMENTS 3,176,042 A    3/1965  Patterson
8,957,250 B2   2/2015  Dongare et al.
(Continued)

FOREIGN PATENT DOCUMENTS

EP    2836476 A2       2/2015
WO    2013/126375 A1   8/2013
WO    WO-2017165323 A1 * 9/2017 ............... B01J 8/02

OTHER PUBLICATIONS

Christian Bruckmeier et al., "Formation of Methyl Acrylate from CO2 and Ethylene via Methylation of Nickelalactones", Organometallics, 29(10): 2199-2202 (2010).
(Continued)

*Primary Examiner* — Deborah D Carr
(74) *Attorney, Agent, or Firm* — Merchant & Gould P.C.

(57) ABSTRACT

A method is for preparing acrylic acid from β-propiolactone and for using β-propiolactone. The process is based on a specific reactivity of β-propiolactone whereby acrylic acid is formed under operating conditions that are mild, especially in terms of temperature.

10 Claims, 2 Drawing Sheets

(51) Int. Cl.
    *B01J 20/28*     (2006.01)
    *B01J 20/32*     (2006.01)
    *B01J 27/08*     (2006.01)
    *C02F 1/28*     (2023.01)
    *C07C 51/44*     (2006.01)
    *C08F 255/02*     (2006.01)
    *C09K 3/32*     (2006.01)
    *D06M 13/203*     (2006.01)
    *D06M 101/20*     (2006.01)

(52) U.S. Cl.
CPC ......... *B01J 20/321* (2013.01); *B01J 20/3217* (2013.01); *B01J 20/3278* (2013.01); *B01J 20/3293* (2013.01); *B01J 27/08* (2013.01); *C02F 1/288* (2013.01); *C07C 51/44* (2013.01); *C08F 255/02* (2013.01); *C09K 3/32* (2013.01); *D06M 13/203* (2013.01); *C02F 1/285* (2013.01); *D06M 2101/20* (2013.01); *D06M 2200/00* (2013.01)

(58) Field of Classification Search
CPC ................ B01J 20/3217; B01J 20/3278; B01J 20/3293; B01J 27/08; C02F 1/288; C02F 1/285; C08F 255/02; C09K 3/32; D06M 13/203; D06M 2101/20; D06M 2200/00
See application file for complete search history.

(56) References Cited

U.S. PATENT DOCUMENTS

2016/0130208 A1     5/2016     Schäffner et al.
2018/0133705 A1     5/2018     Albert et al.

OTHER PUBLICATIONS

International Search Report for PCT/EP2021/063014 (Aug. 2, 2021).

* cited by examiner

METHOD FOR PREPARING ACRYLIC ACID FROM BETA- PROPIOLACTONE

This application is a National Stage Application of PCT/EP2021/063014, filed May 17, 2021, which claims benefit of Patent Application No. 2005098, filed May 19, 2020 in France, and which applications are incorporated herein by reference. To the extent appropriate, a claim of priority is made to each of the above-disclosed applications.

TECHNICAL FIELD OF THE INVENTION

The present invention relates to a method for preparing acrylic acid from propiolactone and the uses thereof.

The method of the invention is based on a specific reactivity of the β-propiolactone which, under operating conditions that are mild, especially in terms of temperature, selectively leads to the formation of acrylic acid.

TECHNICAL BACKGROUND

Acrylic acid is the simplest and most common of α acids, β-unsaturates, it is broadly used on an industrial scale. This resource has been produced at a rate of 5.94 Mt in 2014 and the application has seen a progression each year. Acrylic acid is mainly used for producing super-absorbent materials, formulating resins and paints, but also as an intermediary for synthesising monomers, making it possible to diversify the applications thereof.

The method for industrially synthesising acrylic acid is based mainly on the oxidation of propylene, coming from petrochemistry. The increase in price of acrylic acid in Europe is correlated to the price of propylene. The latter has seen an increase in the price thereof of 60% between 2013 and 2014, which requires the development of new technologies and synthesis methods, as schematised in [FIG. 1].

There is an increasing number of publications about the formation of acrylic acid from lactic acid, or also glycerol in order to move away from products coming from petroleum (R. Beerthuis etal., *Green Chem.* 2015, 17, 1341-1361).

Other methods for synthesising acrylic acid, some of which use β-propiolactone have been described in literature. These different synthesis methods are as follows.

Traditional Method for Synthesising Acrylic Acid by Oxidation of Propylene

The production of acrylic acid today mainly uses the method of synthesis in two steps in a gas phase, which consumes a lot of energy, such as described in (a) K. Weissermel and H. J. Arpe, *Industrial Organic Chemistry*, Wiley-VCH, Weinheim, 2003; (b) H. A. Wittcoff, B. G. Reuben and J. S. Plotkin, *Industrial Organic Chemicals*, Wiley-VCH, Weinheim, 2012. The first step is based on the oxidation of propylene in acrolein using a Bismuth- and Molybdenum-based catalyst (Bi/Mo-O) at 320° C. The intermediary thus formed is then directly converted into acrylic acid using a second oxidation involving a Bismuth- and Vanadium-based catalyst (Bi/V-O) at 280° C.

Synthesis of Acrylic Acid from Lactones or Similar

Use of Brøonsted acid ($H_3PO_4$) described in U.S. Pat. No. 3,176,042.

Historically, the formation of acrylic acid was achieved with a Brønsted acid ($H_3PO_4$ or $P_2O_5$—$H_2O$) from propiolactone. This synthesis method has been abandoned due to the technical problems encountered (corrosive catalyst), of low activity and of adding water for the catalysis.

Polymerisation followed by pyrolysis described in WO 2013/126375.

The company Novomer achieves the synthesis of acrylic acid in two steps. The first step is a step of polymerising propiolactone for obtaining a polyester. This is then pyrolysed to obtain acrylic acid. This two-step system requires heating polymer, under vacuum (>150° C.). This strategy makes it possible to obtain an anhydrous acrylic acid and with an increased purity. However, the synthesis is achieved in two steps and involves a high energy consumption (heating of the polymer, under vacuum).

Use of zeolite (Lewis acid) described in WO 2017/165323.

Novomer has demonstrated the effectiveness of the use of zeolites for the formation of acrylic acid from β-propiolactone. This method however requires a temperature greater than 100° C. in order to avoid secondary reactions, the addition of polymerisation inhibitor is necessary to preserve an increased selectivity.

Use of molten salt from lactide described in US2018133705A1.

Jakob Albert has demonstrated the use of molten salt in the form)(X, where Y is a spectator cation and X is a halide, with the use of an acid catalyst in the form HX or also the use of a reactional intermediary (3-halogenopropionic acid or 2-halogenoprioionic acid). The method however requires a significant heating greater than 150° C. and long times of several hours to a few days which are not in accordance with the use of propiolactone which is not very stable at this temperature.

Dehydration of lactic acid, in particular described in U.S. Pat. No. 8,957,250 and EP 2836476.

The dehydration of the lactic acid in acrylic acid is well-known and described in a consequence number of publications and patent applications, with a broad variety of catalysts. This method consumes a lot of energy with generally high reaction temperatures (around 300° C.). To this selectivity problems are added (selectivity of 80% for the best systems).

Despite the significant number of acrylic acid synthesis methods described in the state of the art, none are totally satisfactory from an energy, environmental and industrial standpoint.

There is therefore a real need for a method making it possible to prepare acrylic acid, which is effective, technically and economically viable, industrially safe and which uses an easily accessible and inexpensive raw material.

There is also a real need for a method for preparing acrylic acid, which is effective, and which does not require strict operating conditions, in particular high temperatures.

Furthermore, there is a real need for a method for preparing acrylic acid such as described above, which brings into play an effective catalyst, available in abundance, inexpensive and non-corrosive.

SUMMARY OF THE INVENTION

The present invention specifically aims to meet these needs by providing a method for preparing acrylic acid from β-propiolactone, characterised in that β-propiolactone is put in contact with a catalyst of formula (I):

$$YX \quad (I)$$

wherein

Y represents an alkaline metal cation, quaternary ammonium of formula $[NR^1R^2R^3R^4]^+$, wherein $R^1$, $R^2$, $R^3$ and $R^4$, identical or different, represent a hydrogen atom, an alkyl radical comprising 1 to 12 carbon atoms, an aryl radical comprising 6 to 20 carbon atoms, said alkyl and aryl radicals being possibly substituted, phosphonium of formula [PR$^1$R$^2$R$^3$R$^4$]$^+$, wherein R$^1$, R$^2$, R$^3$ and R$^4$, identical or different, represent a hydrogen atom, an alkyl radical comprising 1 to 12 carbon atoms, an aryl radical comprising 6 to 20 carbon atoms, said alkyl and aryl radicals being possibly substituted, X is a halide anion chosen from among chloride (Cl$^-$), bromide (Br$^-$) and iodide (I$^-$); and at a temperature less than 100° C.

The method of the invention makes it possible to use β-propiolactone as a precursor of acrylic acid. β-propiolactone can be produced by carbonylation of ethylene oxide, deriving from the oxidation of ethylene, the latter could be biosourced or petrosourced. β-propiolactone can also be obtained from formaldehyde and cetene. It is also available commercially.

The method of the invention is based on a specific reactivity of β-propiolactone which, under operating conditions that are mild, in particular in terms of temperature, selectively leads to the formation of acrylic acid. Indeed, the inventors have observed, in an absolutely unexpected way, that the same mild operating conditions applied to other lactones were totally ineffective.

As shown in [FIG. 2], under operating conditions according to the invention, in particular in terms of catalyst, solvent, time and reaction temperature, the lactide is not at all transformed and β-butyrolactone of which the structure only differs from that of β-propiolactone by the presence of a methyl group, undergoes a decarboxylation reaction to form propylene and CO$_2$.

Another aim of the invention is the use of a method for preparing acrylic acid from β-propiolactone according to the invention, in the production:
  of super-absorbent materials,
  of layers,
  of synthetic rubbers,
  of plastic materials,
  of coatings,
  of paints,
  of ink,
  of organic glasses,
  of glues,
  of acrylic fibres,
  of synthetic leathers,
  of pharmaceutical products,
  of pesticides,
  of fertilisers,
  of detergents,
  of reagents for fine chemistry,
  of an intermediary for producing acrylic esters, and
  of acrylic polymers and copolymers.

The invention also relates to a method for producing super-absorbent materials, layers, synthetic rubbers, plastic materials, coatings, paints, ink, organic glasses, glues, acrylic fibres, synthetic leathers, pharmaceutical products, pesticides, fertilisers, detergents, reagents for fine chemistry, an intermediary for producing acrylic esters, and acrylic polymers and copolymers, characterised in that it comprises:
  (i) a step of preparing acrylic acid from β-propiolactone by the method according to the invention, and possibly
  (ii) a step of separating acrylic acid, for example, by distillation.

The method of the invention can be used in the depollution of water (https://surfacechemistry.nouryon.comn/Site-Assets/pdfs/techbulletin-water-treatment-product-selection-guide-global-2.pdf; https://grandviewresearchinc.blogspot.com/2017/12/polyacrylic-acid-based-polymers-to-simplify-industrial-waste-water-treatment.html).

The invention furthermore aims for a method for functionalising polypropylene (PP)-based technical textiles, intended for the depollution of water, characterised in that it comprises a step of preparing acrylic acid from β-propiolactone by the method according to the invention. The use of technical textiles thus functionalised makes it possible to retain metal trace elements like cadmium, chromium, lead, copper, zinc, mercury, nickel, etc., present in the aqueous environment.

BRIEF DESCRIPTION OF THE FIGURES

Other features and advantages of the invention will appear upon reading the detailed description below for the understanding of which the accompanying figures will be referred to, wherein.

DETAILED DESCRIPTION OF THE INVENTION

Figure 1:
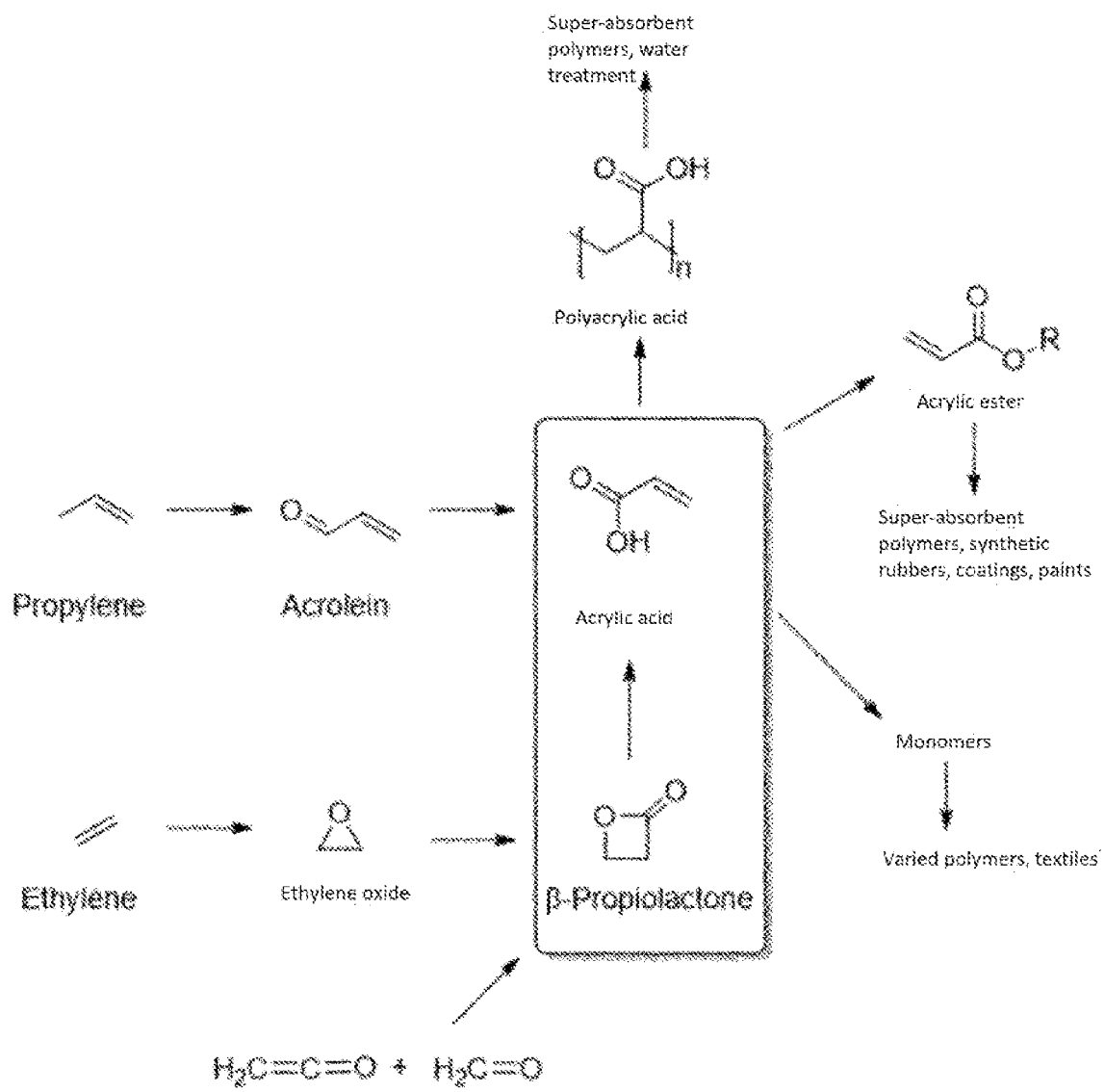
FIG. 1 represents a diagram for producing and using acrylic acid such as described in T. Bonnotte et al., *ChemBioEng Rev* 2018,5, No. 1, 34-56; R. Beerthuis et al., *Green Chem,* 2015, 17, 1341 (Propylene to Acrylic Acid+Applications); V. Mahadevan etal., *Angew. Chem. Int. Ed.* 2002, 41 (15), 2781-2784 (Ethylene oxide to β-propiolactone); Ethylene Oxide—S. Rebsdat et al., *Ullmann's encyclopedia of industrial chemistry,* 2012 (Ethylene to Ethylene Oxide); Hydroxycarboxylic Acids, Aliphatic—J. Miltenberher, *Ullmann's encyclopedia of industrial chemistry,* 2012 (Cetene to β-propiolactone).
Figure 2:
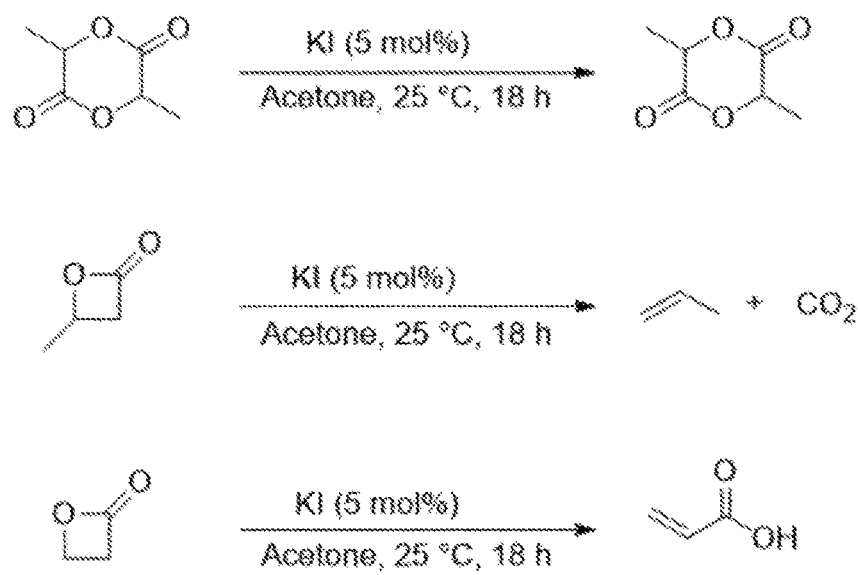
FIG. 2 shows the inventive character and the specificity of the method for preparing acrylic acid from β-propiolactone according to the invention. The operating conditions (catalyst, solvent, reaction time, reaction temperature) which make it possible to obtain acrylic acid from β-propiolactone, have proved to be totally ineffective with other lactones, in particular lactide and β-butyrolactone, of which the structure only differs from that of β-propiolactone by the presence of a methyl group. Lactide does not react and β-butyrolactone undergoes a decarboxylation reaction to form propylene and CO$_2$.

The present invention relates to a method for preparing acrylic acid from β-propiolactone, characterised in that β-propiolactone is put in contact with a catalyst of formula (I):

$$YX \qquad (I)$$

wherein
Y represents an alkaline metal cation, quaternary ammonium of formula [NR$^1$R$^2$R$^3$R$^4$]$^+$, wherein R$^1$, R$^2$, R$^3$ and R$^4$, identical or different, represent a hydrogen atom, an alkyl radical comprising 1 to 12 carbon atoms, an aryl radical comprising 6 to 20 carbon atoms, said alkyl and aryl radicals being possibly substituted, phosphonium of formula [PR$^1$R$^2$R$^3$R$^4$]$^+$, wherein R$^1$, R$^2$, R$^3$ and R$^4$, identical or different, represent a hydrogen atom, an alkyl radical comprising 1 to 12 carbon atoms, an aryl radical comprising 6 to 20 carbon atoms, said alkyl and aryl radicals being possibly substituted, X is a halide anion chosen from among chloride (Cl⁻), bromide (Br⁻) and iodide (I⁻); and at a temperature less than 100° C.

By "alkyl", this means, in the sense of the present invention, a linear carbon radical, ramified or cyclical, saturated, possibly substituted, comprising 1 to 12 carbon atoms, for example 1 to 8 carbon atoms, for example 1 to 6 carbon atoms. Under saturated, linear or ramified alkyl, for example methyl, ethyl, propyl, butyl, pentyl, hexyl, octyl, nonyl, decyl, undecyl, dodecanyl radicals and their ramified isomers can be cited. As cyclic alkyl, cyclopropyl, cyclobutyl, cyclopentyl, cyclohexyl, bicyclo[2,1,1] hexyl, bicyclo[2,2,1] heptyl can be cited, The term "aryl" means a cyclic aromatic substitute comprising 6 to 20 carbon atoms. The aryl group can comprise, for example, 6 to 10 carbon atoms. The aryl group can comprise, for example, 6 carbon atoms. For information, phenyl, benzyl, naphthyl, o-tolyl, m-tolyl, p-tolyl, mesityl, p-nitrophenyl, o-methoxyphenyl, m-methoxyphenyl and p-methoxyphenyl, o-methoxybenzyl, p-methoxybenzyl, m-methoxybenzyl, o-methylbenzyl, p-methylbenzyl and m-methylbenzyl groups can be cited.

Alkyl and aryl radicals can be possibly substituted by one or more alkoxy groups (—O-alkyl); one or more halogen atoms chosen from among fluor, chlorine, bromine and iodine atoms; one or more nitro groups (—NO₂); one or more nitrile groups (—CN); one or more alkyl radicals, one or more aryl radicals, with alkyl and aryl such as defined in the scope of the present invention.

In the catalyst implemented in the method of the invention, X is a halide anion chosen from among chloride (Cl⁻), bromide (Br⁻) and iodide (I⁻). According to a preferred embodiment of the invention, X is a bromide anion. According to another preferred embodiment of the invention, X is an iodide anion.

When Y is an alkaline metal cation, it can be chosen from among Li⁺, Na⁺, K⁺, and Cs⁺.

According to a preferred embodiment of the invention, the alkaline metal cation is K⁺.

According to another preferred embodiment of the invention, the alkaline metal cation is Cs⁺.

When is a quaternary ammonium cation of formula $[NR^1R^2R^3R^4]^+$, $R^1$, $R^2$, $R^3$ and $R^4$, identical or different, can represent a hydrogen atom, an alkyl radical comprising 1 to 8 carbon atoms, an aryl radical comprising 6 to 10 carbon atoms, said alkyl and aryl radicals being possibly substituted.

According to a preferred embodiment of the invention, Y is a quaternary ammonium cation of formula $[NR^1R^2R^3R^4]^+$, wherein $R^1$, $R^2$, $R^3$ and $R^4$ represent an alkyl radical chosen from among methyl, ethyl, propyl, butyl, pentyl, hexyl, heptyl, and their ramified isomers; a phenyl radical chosen from among phenyl, benzyl, naphthyl, said alkyl and aryl radicals being possibly substituted. In this embodiment, Y is advantageously [N(n-Bu)₄]⁺. When Y is a phosphonium cation of formula $[PR^1R^2R^3R^4]^+$, $R^1$, $R^2$, $R^3$ and $R^4$, identical or different, can represent a hydrogen atom, an alkyl radical comprising 1 to 8 carbon atoms, an aryl radical comprising 6 to 10 carbon atoms, said alkyl and aryl radicals being possibly substituted.

According to a preferred embodiment of the invention, Y is a phosphonium cation of formula $[PR^1R^2R^3R^4]^+$, $R^1$, $R^2$, $R^3$ and $R^4$, wherein $R^1$, $R^2$, $R^3$ and $R^4$ represent an alkyl radical chosen from among methyl, ethyl, propyl, butyl, pentyl, hexyl, heptyl, and their ramified isomers; a phenyl radical chosen from among phenyl, benzyl, naphthyl, said alkyl and aryl radicals being possibly substituted. In this embodiment, Y is advantageously [PPh₄]⁺.

From among the preferred catalysts, in particular LiI, NaI, KI, KCl, KBr, CsI, [N(n-Bu)₄]I, [PPh₄]I can be cited.

The catalyst can, if necessary, be immobilised on a heterogenous support, for example, in order to ensure an easy separation of said catalyst and/or the recycling thereof. Said heterogenous support can be chosen from among the silica gel or cationic polymer-based supports, like for example, poly(ethyleneimine), (PEI), poly-L-(lysine) (PLL), or based on polysaccharides.

The catalyst can be a solid polymer support, like that available at Sigma Aldrich, under the reference Sigma-Aldrich-572942, in particular for ammonium and phosphonium cations, or that described in https://onlinelibrary.wiley.com/doi/abs/10.1002/app.35297 (Iodination of stable aromatic diazonium salt using crosslinked poly (4-vinylpyridine)-supported iodide), or also that described in https://pubs.acs.org/doi/abs//10.1021/acs.macromol.9b02266 (Recyclable Solid-Supported Catalysts for Quaternary Ammonium Iodide-Catalyzed Living Radical Polymerization).

The catalysts used in the method of the invention which are halide salts such as described above, have a low cost. A large portion of these catalysts are solids with low or zero toxicities and easy to use.

The method of the invention, in particular, the putting in contact of β-propiolactone with the catalyst of formula (I), can occur in the absence of solvent. In this case, the presence of a polymerisation inhibitor as those described below, could prove to be advantageous.

The method of the invention, in particular, the putting in contact of β-propiolactone with the catalyst of formula (I), can also occur in one or a mixture of at least two solvent(s). The solvents used can be anhydrous or non-anhydrous. The solvents which can react with β-propiolactone or acrylic acid are to be avoided.

In the scope of the invention, the solvent can be chosen from among:

- ethers, linear or cyclic, chosen from the group constituted by diethylic ether, dibutylether, THF, 2-methyl THF, dioxane and diglyme;
- esters, linear or cyclic, chosen from the group constituted by methyl acetate, ethyl acetate, propyl acetate, isopropyl acetate, n-butyl acetate, isobutyl acetate, ethyl acetate, Y-butryolactone, dimethyl adipate, dimethyl glutarate, dimethyl succinate;
- ketones, linear or cyclic, α-butryolactone s, chosen from the group constituted by acetone or propanone, butanone or methylethylketone, 4-methyl-2-pentanone or methyllisobutylketone, acetophenone, phenylmethylketone, cyclohexanone, isophorone, N-methylpyrrolidone;
- starches, linear or cyclic, chosen from the group constituted by formamide, N-methylformamide, N, -dimethylformamide (DMF), acetamide, N-methylacetamide, N,N-dimethylacetamide N-methyl-2-pyrrolidone (NMP);
- sulfoxides like dimethylesulfoxide;
- aromatic hydrocarbons chosen from the group constituted by benzene, toluene, xylene (ortho, meta, pura), ethylbenzene, cumene or isopropylbenzene, mesitylene or 1,3,5-trimethylbenzene;
- nitriles, linear or cyclic, chosen from the group constituted by acetonitrile, propanitrile, acrylonitrile, benzonitrile, butyronitrile, decanonitrile, isobutyronitrile, pivalonitrile, valeronitrile;

alkyl halides chosen from among the group constituted by chloroform, dichloromethane, carbon tetrachloride, methylene chloride.

In an embodiment of the invention, the solvent can be chosen from among:
- ethers, linear or cyclic, chosen from the group constituted by diethylic ether, dibutylether, THF, 2-methyl THF, dioxane and diglyme;
- esters, linear or cyclic, chosen from the group constituted by methyl acetate, ethyl acetate, propyl acetate, isopropyl acetate, n-butyl acetate, isobutyl acetate, ethyl acetate, Y-butryolactone, dimethyl adipate, dimethyl glutarate, dimethyl succinate;
- ketones, linear or cyclic, α-butryolactone s, chosen from the group constituted by acetone or propanone, butanone or methylethylketone, 4-methyl-2-pentanone or methyllisobutylketone, acetophenone, phenylmethylketone, cyclohexanone, isophorone, N-methylpyrrolidone;
- starches, linear or cyclic, chosen from the group constituted by formamide, N-methylformamide, N,N-dimethylformamide (DMF), acetamide, N-methylacetamide, N,N-dimethylacetamide N-methyl-2-pyrrolidone (NMP);
- nitriles, linear or cyclic, chosen from the group constituted by acetonitrile, propanitrile, acrylonitrile, benzonitrile, butyronitrile, decanonitrile, isobutyronitrile, pivalonitrile, valeronitrile.

Contrary to current methods for producing acrylic acid from β-propiolactone which involve a high energy consumption (heating, under vacuum, at temperatures greater than 100° C.) in order to distil the product continuously formed, the method for preparing acrylic acid from β-propiolactone according to the invention is carried out under mild conditions, in particular in terms of temperature and of pressure.

Indeed, the temperature at which the method of the invention is implemented is less than or equal to 100° C., preferably less than or equal to 80° C., more preferably less than or equal to 50° C. More specifically, the temperature can be between 10° C. and 80° C. preferably between 15 and 55° C., more preferably between 20 and 45° C.

The implementation of the method of the invention does not require reduced pressure and can be done at atmospheric pressure.

The method can be performed under inert atmosphere (nitrogen, argon, for example) or in air without affecting neither the selectivity nor the activity of the catalyst.

The duration of the method can vary from one hour, even a few hours, to a few days, according to the solvent, the catalyst, the quantity of catalyst, the concentration of β-propiolactone and the temperature. In particular, the duration can be of between 1 hour and 120 hours, preferably between 1 and 80 hours, more preferably between 4 and 20 hours.

The concentration of β-propiolactone in the reactional medium can vary from several mmol·L$^{-1}$ to several mol·L$^{-1}$. It can be between 0.1 and 16 mol·L$^{-1}$, preferably between 0.1 and 10 mol·L$^{-1}$, more preferably between 0.1 and 5 mol·L$^{-1}$.

The catalyst is used in catalytic quantity, i.e. in quantity less than the stoichiometric quantity. The quantity of catalyst can be between 0.01 and 20 mol %, preferably from 0.05 to 15 mol %, more preferably from 1 to 10 mol %, with respect to lactone. The increase in concentration of catalyst makes it possible to decrease the reaction time.

The presence of a low-cost, low-toxicity catalyst, available in abundance and a chemical simplicity is an added value compared with the catalytic systems of the state of the art.

Acrylic acid is very reactive and can achieve explosive polymerisations. The use of concentrations of β-propiolactone of around 1 mol·L$^{-1}$ in a homogenous medium makes it possible to avoid any explosive polymerisation of acrylic acid and enables a simplified purification. With the method of the invention, acrylic acid can be easily purified, if necessary, by distillation techniques known to a person skilled in the art.

The nature of the catalyst makes it possible to easily separate it at the end of reaction without decreasing its activity, after a distillation intended to separate the acrylic acid, the possible impurities and the reaction solvent. The catalyst can also be partially or totally recovered by a simple filtration.

The method of the invention can further occur in the presence of an additive. Thus, the putting in contact of β-propiolactone with the catalyst of formula (I) will occur in the presence of an additive. The additive, which has the role of improving the solubility of the catalyst for the transformation of β-propiolactone, can be chosen from the group constituted by:
- crown ethers chosen from among 12-crown-4, 15-crown-5, 18-crown-6, dibenzo-18-crown-6, benzo-18-crown-6, benzo-15-crown-5, or dibenzo-15-crown-5;
- aza-crowns chosen from among 1,4,7,10-tetraazacyclodoecane (cyclene), 1,4,7,10,13,16-hexaazacyclooctadecane (hexacyclene), or diaza-18-crown-6;
- crown thioethers chosen from among 1,5,9,13-tetrathiacyclohexadecane (16-Ane-S$_4$), or 1,4,7,10,13,16-hexathiacyclooctadecane (18-Ane-S$_6$); or
- cryptands chosen from among [2,1,1], [2,2,1], [2,2,2], [2,2,2]B, [2,2,3], [2,3,3], [3,3,3].

When the method of the invention is performed in the presence of an additive, the quantity of said additive in the reactional medium can be between 0.01 and 20 mol %, preferably between 0.05 and 15 mol %, more preferably between 1 and 10 mol %, with respect to lactone.

The implementation of a method according to the invention does not need any specific reactor.

Figure 3:
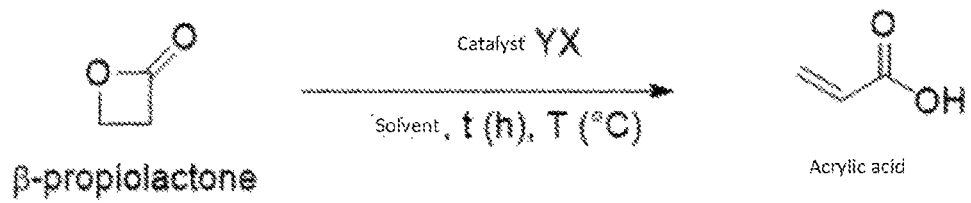
FIG. 3 schematically represents a method for preparing acrylic acid from β-propiolactone according to the invention in the presence of a solvent.

The method for preparing acrylic acid from β-propiolactone in the presence of solvent is schematically represented in [FIG. 3].

The method of the invention enables the preparation of acrylic acid with good yields and a selectivity at least comparable to that of known systems. In certain cases, following the method of the invention, further to the desired product, the only subproduct present in the medium is an oligomer having polyester functions and an olefine end, generally present in the form of a dimer and/or trimer, which makes it possible to use the mixture such as for subsequent applications and operations. However, if necessary, it is possible to easily remove the oligomer from the acrylic acid, for example by a simple distillation.

It must be noted that the oligomer could come from the addition of Michael by reaction of two acrylic acid molecules, or an acrylic acid molecule and a reactional intermediary. Although the method of the invention does not require the presence of a polymerisation inhibitor to obtain a high acrylic acid selectivity, it can be considered to make use of it, in order to avoid secondary polymerisation reactions, and to thus preserve a high selectivity. As already indicated, when the method occurs in the absence of solvent, the presence of a polymerisation inhibitor could prove to be advantageous.

In this regard, for example copper powder, hydroquinone, hydroquinone monomethylether, and phenothiazine can be cited.

The quantity of polymerisation inhibitor can be greater than or equal to 20 ppm, preferably greater than or equal to 50 ppm, more preferably greater than or equal to 100 ppm, also more preferably greater than or equal to 200 ppm.

The mild conditions developed by the method of the invention make it possible to avoid several problems relating, in particular, to the use of β-propiolactone as a starting reagent, and the acrylic acid obtained.

The mild operating conditions of the method of the invention, in particular in terms of temperatures make it possible to avoid the thermal decomposition of β-propiolactone (162° C.).

The mild operating conditions of the method of the invention, in particular in terms of temperatures make it possible to limit the degradation of acrylic acid by the irreversible formation of a dimer by reaction of two acrylic acid molecules. Thus, the good selectivity for the desired product is maintained.

The method of the invention enables a lower energy consumption than the methods of the state of the art.

The possibility of performing below the boiling point of the solvent or of using solvents having a low boiling point (less than 100° C.) is an advantage never obtained with the methods of the state of the art.

Another aim of the invention is the use of a method for preparing acrylic acid from β-propiolactone according to the invention, in the production:
of super-absorbent materials,
of layers,
of synthetic rubbers,
of plastic materials,
of coatings,
of paints,
of ink,
of organic glasses,
of glues,
of acrylic fibres,
of synthetic leathers,
of pharmaceutical products,
of pesticides,
of fertilisers,
of detergents,
of reagents for fine chemistry,
of an intermediary for producing acrylic esters, and
acrylic polymers and copolymers.

The invention also relates to a method for producing super-absorbent materials, layers, synthetic rubbers, plastic materials, coatings, paints, ink, organic glasses, glues, acrylic fibres, synthetic leathers, pharmaceutical products, pesticides, fertilisers, detergents, reagents for fine chemistry, an intermediary for producing acrylic esters, and acrylic polymers and copolymers, characterised in that it comprises:
(i) a step of preparing acrylic acid from -propiolactone by the method according to the invention, and possibly
(ii) a step of separating the acrylic acid, for example, by distillation.

The method of the invention can be used in the depollution of water.

The invention furthermore aims for a method for functionalising polypropylene (PP)-based technical textiles, intended for the depollution of water, characterised in that it comprises a step of preparing acrylic acid from β-propiolactone by the method according to the invention. The use of technical textiles thus functionalised makes it possible to retain metal trace elements like cadmium, chromium, lead, copper, zinc, mercury, nickel, etc., present in the aqueous environment.

Generally, the technical textile, can mean a fabric, non-woven, string, braid, etc., constituted of so-called technical fibres, having features chosen for one or more well-determined applications (depollution of water, for example). According to the application, the fibres can be, for example, carbon, glass, polyester, polypropylene, aramid, polyethylene fibres.

EXAMPLES

1. Preparation of Acrylic Acid from β-Propiolactone According to the Method of the Invention The different reagents and solvents used in the method of the invention and in the examples (β-propiolactone, catalyst, etc.) are, generally, commercial compounds or can be prepared by any method known to a person skilled in the art.

1. In an inert atmosphere or in air, the catalyst (x mol %), β-propiolactone (x' mol·L$^{-1}$) and the solvent (x" mL) are introduced in an RMN tube. In order to monitor the yield of acrylic acid and the conversion of β-propiolactone, an internal standard can be added. The order of introducing the reagent, solvent, internal standard or catalyst has no impact on the reaction.

2. The RMN tube is then placed at a temperature of between 15 and 80° C.

3. The conversion of β-propiolactone and the yield of acrylic add can be monitored in RMN $^1$H (Bruker Avarice Neo 400 MHz) or in GC-MS (Shimadzu GCMS-QP2010 Ultra).

The solvents and the different reagents used in the method of the invention (β-propiolactone, the catalyst, the additive) are, generally, commercial compounds or can be prepared by any method known to a person skilled in the art. The non-anhydrous solvents can be used. The reagents, catalysts, solvents used in the present examples are products commercialised by the company Sigma Aldrich. Different parameters of the method of the invention have been studied. The extent of the variations for each parameter is described below.

The conversions and the yields described are measured in RMN $^1$H thanks to an internal standard added at the start of the reaction, mesitylene. These conversions and yields are measured with an accuracy of around 5%. In the context of the present invention, it is useful to be reminded of the following definitions.

Conversion (%)=(starting quantity of lactone−quantity of lactone not having reacted/starting quantity of lactone)×100.

Yield of acrylic acid (%)=(number of acrylic acid moles formed/starting number of lactone moles)×100.

Yield of oligomer(s) (%)=(quantity of oligomer(s) formed/starting quantity of lactone)×100.

Selectivity (%)=(yield of acrylic acid formed/conversion)×100.

Example 1

Potassium iodide (4.1mg, 0.025mmol, 0.05eq), β-propiolactone (31 μL, 0.500 mmol, 1 eq) and acetone-d$_6$ (500 μL) are added in a sealed tube. Finally, mesitylene (14 μL, 0.100 mmol, 0.1 eq) is added as an internal standard. The reaction is stirred for 112 hours at 20° C.

Example 2

Potassium iodide (4.1 mg, 0.025 mmol, 0.05 eq), β-propiolactone (31 μL, 0.500 mmol, 1 eq) and acetone-$d_6$ (500 μL) are added in a sealed tube. Finally, mesitylene (14 μL, 0.100 mmol, 0.1 eq) is added as an internal standard. The reaction is stirred for 16 hours at 45° C.

Example 3

Potassium iodide (1.0 mg, 0.006 mmol, 0.05 eq), β-propiolactone (7.75 μL, 0.125 mmol, 1 eq) and acetone-$d_6$ (500 μL) are added in a sealed tube. Finally, mesitylene (3.5 μL, 0.025 mmol, 0.1 eg) is added as an internal standard. The reaction is stirred for 16 hours at 45° C.

Example 4

Potassium iodide (4.1 mg, 0.025 mmol, 0.05 eq), crown ether (18-c-6) (6.6 mg, 0.025 mmol, 0.05 eq), β-propiolactone (31 μL, 0.500 mmol, 1 eq) and acetone-$d_6$ (500 μL) are added in a sealed tube. Finally, mesitylene (14 μL, 0.100 mmol, 0.1 eq) is added as an internal standard. The reaction is stirred for 16 hours at 45° C.

Example 5

Potassium iodide (41 mg, 0.025 mmol, 0.05 eq), β-propiolactone (310 μL, 5 mmol, 1 eq) and acetone-$d_6$ (5 ml) are added in a single-neck flask. Finally, mesitylene (14 μL, 0.100 mmol, 0.1 eq) is added as an internal standard. The reaction is stirred for 10 hours at 45° C. for a conversion of 99% with a selectivity of 73%.

2. Impact of Different Parameters on the Production of Acrylic Acid 2.1. Solvent Test The impact of the solvent on the production of acrylic acid has been studied. To this end, the method of the invention has been performed with a wide range of solvents according to the diagram below at 20 or 45° C. [Table 1] summarised the results obtained.

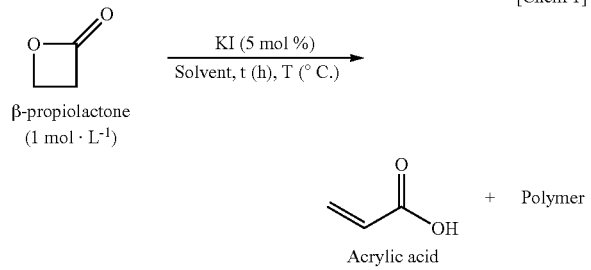

[Chem 1]

TABLE 1

| Solvent | T (° C.) | t (h) | β-propiolactone Conversion (%) | Acrylic acid Yield (%) | Oligomer Yield (%) | Selectivity (%) |
|---|---|---|---|---|---|---|
| Acetone-$d_6$ | 45 | 1 | 17 | 11 | 6 | 65 |
| Acetone-$d_6$ | 45 | 16 | 100 | 82 | 18 | 82 |
| Acetone-$d_6$ | 45 | 64 | 100 | 68 | 32 | 68 |
| Acetone-$d_6$ | 20 | 64 | 77 | 55 | 22 | 72 |
| Acetone-$d_6$ | 20 | 88 | 87 | 64 | 23 | 74 |
| Acetone-$d_6$ | 20 | 112 | 94 | 72 | 22 | 77 |
| EtOAc | 45 | 1 | 4 | 4 | 0 | 100 |
| EtOAc | 45 | 16 | 36 | 22 | 14 | 61 |
| DMF | 45 | 1 | 40 | 19 | 20 | 49 |
| DMF | 45 | 16 | 100 | 39 | 61 | 39 |
| DMF | 20 | 64 | 100 | 46 | 54 | 46 |
| DMF | 20 | 88 | 100 | 47 | 53 | 47 |
| DMF | 20 | 112 | 100 | 47 | 53 | 47 |
| DMSO-$d_6$ | 45 | 1 | 39 | 18 | 21 | 46 |
| DMSO-$d_6$ | 45 | 16 | 61 | 26 | 34 | 43 |
| Toluene-$d_8$ | 45 | 16 | 29 | 0 | 29 | 0 |
| $CD_3CN$ | 45 | 1 | 12 | 5 | 7 | 44 |
| $CD_3CN$ | 45 | 16 | 79 | 38 | 41 | 49 |
| $CD_3CN$ | 20 | 64 | 44 | 25 | 19 | 57 |
| $CD_3CN$ | 20 | 88 | 51 | 28 | 23 | 55 |
| $CD_3CN$ | 20 | 112 | 57 | 31 | 25 | 55 |
| THF-$d_8$ | 45 | 1 | 3 | 2 | 1 | 67 |
| THF-$d_8$ | 45 | 16 | 11 | 8 | 3 | 70 |
| DME | 45 | 1 | 2 | 1 | 1 | 57 |
| DME | 45 | 18 | 88 | 45 | 23 | 66 |
| DME | 20 | 64 | 59 | 39 | 19 | 67 |
| DME | 20 | 88 | 65 | 45 | 21 | 68 |
| DME | 20 | 112 | 70 | 48 | 22 | 68 |

Under the operating conditions indicated in [Table 1], the best solvent tested was revealed to be acetone. However, it is possible to use other solvents like, for example, DME, acetonitrile, THF, DMSO, DMF and ethyl acetate.

2.2. Additive Test

The impact of adding an additive on the production of acrylic acid has been studied. To this end, the method of the invention has been performed in the presence of the crown ether 18-c-6 (18-crown-6) at 5 mol % as additive, according to the diagram below at 20 to 45° C. [Table 2] summarises the results obtained.

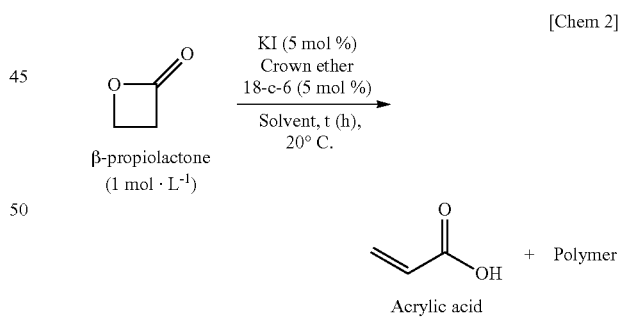

[Chem 2]

TABLE 2

| Solvent | t (h) | β-propiolactone Conversion (%) | Acrylic acid Yield (%) | Oligomer Yield (%) | Selectivity (%) |
|---|---|---|---|---|---|
| Acetone-$d_6$ | 15 | 63 | 30 | 33 | 48 |
| Acetone-$d_6$ | 39 | 96 | 60 | 36 | 62 |
| EtOAc | 15 | 48 | 15 | 33 | 32 |
| EtOAc | 39 | 69 | 24 | 45 | 35 |
| $CD_2Cl_2$ | 15 | 55 | 6 | 49 | 11 |
| DMF | 15 | 48 | 20 | 28 | 42 |

TABLE 2-continued

| Solvent | t (h) | β-propiolactone Conversion (%) | Acrylic acid Yield (%) | Oligomer Yield (%) | Selectivity (%) |
|---|---|---|---|---|---|
| DMF | 39 | 100 | 39 | 61 | 39 |
| DMSO-d$_6$ | 15 | 23 | 5 | 18 | 20 |
| DMSO-d$_6$ | 39 | 31 | 9 | 23 | 27 |
| CD$_3$CN | 15 | 30 | 8 | 22 | 27 |
| CD$_3$CN | 39 | 50 | 17 | 33 | 34 |
| THF-d$_8$ | 15 | 93 | 48 | 45 | 52 |
| THF-d$_8$ | 39 | 100 | 56 | 44 | 56 |
| DME | 15 | 73 | 36 | 37 | 50 |
| DME | 39 | 100 | 63 | 37 | 63 |

The addition of a crown ether therefore makes it possible to substantially increase the reactivity. However, under the operating conditions indicated in [Table 2], a loss of selectivity is observed with respect to the results obtained at 20 and 45° C. without crown ether in [Table 1].

2.3. Cation (Y) Nature of the Catalyst Test

The impact of the cation (Y) nature of the catalyst on the production of acrylic acid has been studied. To this end, the method of the invention has been performed with catalysts comprising different cations (Y) at 5 mol %, according to the diagram below, at 45° C. [Table 3] summarises the results obtained.

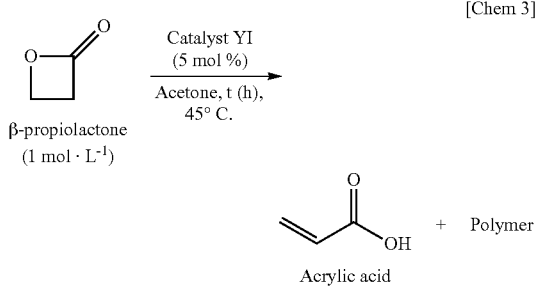

[Chem 3]

TABLE 3

| Catalyst (mol %) | t (h) | β-propiolactone Conversion (%) | Acrylic acid Yield (%) | Oligomer Yield (%) | Selectivity (%) |
|---|---|---|---|---|---|
| KI (5) | 1 | 17 | 11 | 6 | 65 |
| KI (5) | 16 | 100 | 82 | 18 | 82 |
| LiI (5) | 1 | 1 | 1 | 0 | 100 |
| LiI (5) | 16 | 16 | 16 | 0 | 100 |
| NaI (5) | 1 | 2 | 2 | 0 | 100 |
| NaI (5) | 16 | 39 | 30 | 9 | 77 |
| CsI (5) | 1 | 13 | 3 | 10 | 23 |
| CsI (5) | 16 | 100 | 63 | 37 | 63 |
| n-NBu$_4$I (5) | 1 | 50 | 17 | 33 | 34 |
| n-NBu$_4$I (5) | 16 | 100 | 62 | 38 | 62 |
| PPh$_4$I (5) | 1 | 38 | 9 | 29 | 24 |
| PPh$_4$I (5) | 16 | 100 | 60 | 40 | 60 |

According to the results obtained, it seems clearly that the cations have an impact on the activity and the selectivity of the method. Under the operating conditions indicated in [Table 3], potassium has shown a good activity/selectivity ratio.

2.4. Anion (X) Nature of the Catalyst Test

The impact of the anion (X) nature of the catalyst on the production of acrylic acid has been studied. To this end, the method of the invention has been performed with catalysts comprising different anions (X) at 5 mol %, according to the diagram below, at 45° C. [Table 4] summarises the results obtained.

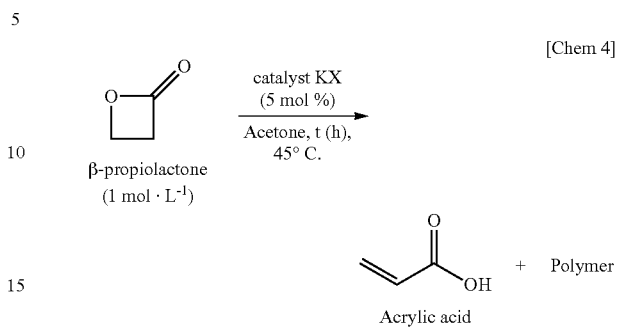

[Chem 4]

TABLE 4

| Catalyst (mol %) | t (h) | β-propiolactone Conversion (%) | Acrylic acid Yield (%) | Oligomer Yield (%) | Selectivity (%) |
|---|---|---|---|---|---|
| KI (5) | 1 | 17 | 11 | 6 | 65 |
| KI (5) | 16 | 100 | 82 | 18 | 82 |
| KBr (5) | 16 | 29 | 7 | 22 | 23 |
| KCl (5) | 16 | 12 | 2 | 10 | 14 |

According to the results obtained, it seems clearly that anions have an impact on the activity of the selectivity of the method. Under the operating conditions indicated in [Table 4], iodine has shown a good activity/selectivity ratio.

2.5. Catalyst Concentration Test

The impact of the catalyst concentration on the production of acrylic acid has been studied. To this end, the method of the invention has been performed with potassium iodide (KI) as catalyst with different concentrations expressed in mol % with respect to β-propiolactone, according to the diagram below, at 45° C. [Table 5] summarises the results obtained.

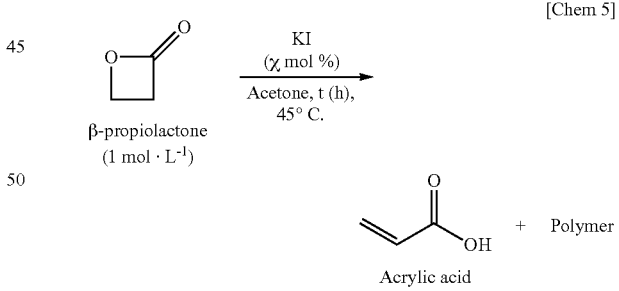

[Chem 5]

TABLE 5

| Catalyst (mol %) | t (h) | β-propiolactone Conversion (%) | Acrylic acid Yield (%) | Oligomer Yield (%) | Selectivity (%) |
|---|---|---|---|---|---|
| KI (1) | 1 | 8 | 4 | 4 | 50 |
| KI (1) | 16 | 55 | 12 | 43 | 22 |
| KI (3) | 1 | 13 | 7 | 6 | 57 |
| KI (3) | 16 | 90 | 53 | 37 | 59 |
| KI (5) | 1 | 17 | 11 | 6 | 65 |
| KI (5) | 16 | 100 | 82 | 18 | 82 |

TABLE 5-continued

| Catalyst (mol %) | t (h) | β-propiolactone Conversion (%) | Acrylic acid Yield (%) | Oligomer Yield (%) | Selectivity (%) |
|---|---|---|---|---|---|
| KI (10) | 1 | 22 | 12 | 10 | 55 |
| KI (10) | 16 | 100 | 72 | 28 | 72 |

According to these results, the catalyst concentration can be modified to make the reaction time vary. Under the operating conditions indicated in [Table 5], the selectivity seems to be impacted by the catalyst concentration.

2.6. β-Propiolactone Concentration Test

The impact of β-propiolactone concentration on the production of acrylic acid has been studied. To this end, the method of the invention has been performed with different β-propiolactone concentrations, according to the diagram below, at 4.5° C. [Table 6] summarises the results obtained.

[Chem 6]

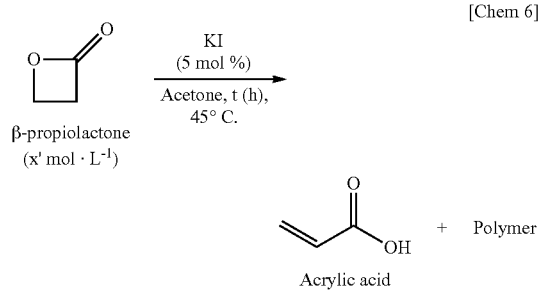

TABLE 6

| Concentration (mol·L$^{-1}$) | t (h) | β-propiolactone Conversion (%) | Acrylic acid Yield (%) | Oligomer Yield (%) | Selectivity (%) |
|---|---|---|---|---|---|
| 0.25 | 1 | 24 | 10 | 14 | 44 |
| 0.25 | 16 | 100 | 84 | 16 | 84 |
| 1 | 1 | 17 | 11 | 6 | 65 |
| 1 | 16 | 100 | 82 | 18 | 82 |
| 4 | 1 | 27 | 12 | 15 | 44 |
| 4 | 16 | 100 | 59 | 41 | 59 |

These results show that the β-propiolactone concentration has an impact on the method of the invention. Indeed, under the operating conditions indicated in [Table 6], the selectivity falls rapidly when the concentration is greater than 1 mol·L$^{-1}$.

The invention claimed is:

1. A method for preparing acrylic acid from β-propiolactone, wherein β-propiolactone is put in contact with a catalyst of formula (I):

YX          (I)

wherein
Y represents a cation
of alkaline metal,
quaternary ammonium of formula [NR$^1$R$^2$R$^3$R$^4$]$^+$, wherein R$^1$, R$^2$, R$^3$ and R$^4$, identical or different, represent a hydrogen atom, an alkyl radical comprising 1 to 12 carbon atoms, an aryl radical comprising 6 to 20 carbon atoms, said alkyl and aryl radicals being substitutable,
phosphonium of formula [PR$^1$R$^2$R$^3$R$^4$]$^+$, wherein R$^1$, R$^2$, R$^3$ and R$^4$, identical or different, represent a hydrogen atom, an alkyl radical comprising 1 to 12 carbon atoms, an aryl radical comprising 6 to 20 carbon atoms, said alkyl and aryl radicals being substitutable,
X is a halide anion chosen from among chloride (Cl$^-$), bromide (Br$^-$) and iodide (I$^-$); and
at a temperature less than 100° C.

2. The method according to claim 1, wherein Y is an alkaline metal cation chosen from among Li$^+$, Na$^+$, K$^+$, and Cs$^+$.

3. The method according to claim 1, wherein Y is a quaternary ammonium cation of formula [NR$^1$R$^2$R$^3$R$^4$]$^+$, wherein R$^1$, R$^2$, R$^3$ and R$^4$, identical or different, represent an alkyl radical chosen from among methyl, ethyl, propyl, butyl, pentyl, hexyl, heptyl, and their ramified isomers; a phenyl radical chosen from among phenyl, benzyl, naphthyl; said alkyl and aryl radicals being substitutable.

4. The method according to claim 1, wherein Y is a phosphonium cation of formula [PR$^1$R$^2$R$^3$R$^4$]$^+$, R$^1$, R$^2$, R$^3$ and R$^4$, wherein R$^1$, R$^2$, R$^3$ and R$^4$ represent an alkyl radical chosen from among methyl, ethyl, propyl, butyl, pentyl, hexyl, heptyl, and their ramified isomers; a phenyl radical chosen from among phenyl, benzyl, naphthyl; said alkyl and aryl radicals being substitutable.

5. The method according to claim 1, wherein X is a bromide anion (Br$^-$) or an iodide anion (I$^-$).

6. The method according to claim 1, wherein the putting in contact of β-propiolactone with the catalyst of formula (I) occurs in one or a mixture of at least two solvent(s) chosen from among:

ethers, linear or cyclic, chosen from the group consisting of diethylic ether, dibutylether, THF, 2-methyl THF, dioxane and diglyme;

esters, linear or cyclic, chosen from the group consisting of methyl acetate, ethyl acetate, propyl acetate, isopropyl acetate, n-butyl acetate, isobutyl acetate, ethyl acetate, Y-butryolactone, dimethyl adipate, dimethyl glutarate, dimethyl succinate;

ketones, linear or cyclic, α-butryolactone s, chosen from the group consisting of acetone or propanone, butanone or methylethylketone, 4-methyl-2-pentanone or methyllisobutylketone, acetophenone, phenylmethylketone, cyclohexanone, isophorone, N-methylpyrrolidone;

starches, linear or cyclic, chosen from the group consisting of formamide, N-methylformamide, N,N-dimethylformamide (DMF), acetamide, N-methylacetamide, N,N-dimethylacetamide N-methyl-2-pyrrolidone (NMP);

sulfoxides comprising dimethylesulfoxide;

aromatic hydrocarbons chosen from the group consisting of benzene, toluene, xylene (ortho, meta, pura), ethylbenzene, cumene or isopropylbenzene, mesitylene or 1,3,5-trimethylbenzene;

nitriles, linear or cyclic, chosen from the group consisting of acetonitrile, propanitrile, acrylonitrile, benzonitrile, butyronitrile, decanonitrile, isobutyronitrile, pivalonitrile, valeronitrile;

alkyl halides chosen from among the group consisting of chloroform, dichloromethane, carbon tetrachloride, methylene chloride.

7. The method according to claim 1, wherein the putting in contact of β-propiolactone with the catalyst of formula (I) occurs in the presence of an additive chosen from the group consisting of:

crown ethers chosen from among 12-crown-4, 15-crown-5, 18-crown-6, dibenzo-18-crown-6, benzo-18-crown-6, benzo-15-crown-5, or dibenzo-15-crown-5;

aza-crowns chosen from among 1,4,7,10-tetraazacyclodoecane (cyclene), 1,4,7,10,13,16-hexaazacyclooctadecane (hexacyclene), or diaza-18-crown-6;

crown thioethers chosen from among 1,5,9,13-tetrathiacyclohexadecane (16-Ane-$S_4$), or 1,4,7,10,13,16-hexathiacyclooctadecane (18-Ane-$S_6$); or cryptands chosen from among [2,1,1], [2,2,1], [2,2,2], [2,2,2]B, [2,2,3], [2,3,3], [3,3,3].

8. An use of a method for preparing acrylic acid from β-propiolactone according to claim 1, in the production:

of super-absorbent materials,
of layers,
of synthetic rubbers,
of plastic materials,
of coatings,
of paints,
of ink,
of organic glasses,
of glues,
of acrylic fibres,
of synthetic leathers,
of pharmaceutical products,
of pesticides,
of fertilisers,
of detergents,
of reagents for fine chemistry,
of an intermediary for producing acrylic esters, and
of acrylic polymers and copolymers.

9. A method for producing super-absorbent materials, layers, synthetic rubbers, plastic materials, coatings, paints, glues, acrylic fibres, synthetic leathers, pharmaceutical products, pesticides, fertilisers, detergents, and an intermediary for the synthesis of monomers, which comprises:

(i) a step of preparing acrylic acid from β-propiolactone by the method according to claim 1, and (ii) a step of separating the acrylic acid by distillation.

10. The method for functionalising polypropylene (PP)-based technical textiles for depollution of water, which comprises a step of preparing acrylic acid from β-propiolactone by the method according to claim 1.

* * * * *